United States Patent
Ma et al.

(10) Patent No.: US 9,511,348 B2
(45) Date of Patent: Dec. 6, 2016

(54) FUNCTIONALIZED POROUS ORGANIC POLYMERS FOR OLEFIN/PARAFFIN SEPARATIONS

(71) Applicants: Shengqian Ma, Tampa, FL (US); Baiyan Li, Tampa, FL (US)

(72) Inventors: Shengqian Ma, Tampa, FL (US); Baiyan Li, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/590,385

(22) Filed: Jan. 6, 2015

(65) Prior Publication Data

US 2015/0190779 A1    Jul. 9, 2015

Related U.S. Application Data

(60) Provisional application No. 61/924,506, filed on Jan. 7, 2014.

(51) Int. Cl.

| | | |
|---|---|---|
| *C08J 9/36* | (2006.01) | |
| *B01J 20/22* | (2006.01) | |
| *C07C 7/12* | (2006.01) | |
| *B01J 20/28* | (2006.01) | |
| *B01J 20/30* | (2006.01) | |
| *C08J 5/20* | (2006.01) | |

(52) U.S. Cl.
CPC ......... *B01J 20/223* (2013.01); *B01J 20/28057* (2013.01); *B01J 20/28078* (2013.01); *B01J 20/3085* (2013.01); *C07C 7/12* (2013.01); *C08J 5/20* (2013.01)

(58) Field of Classification Search
CPC .............. B01J 20/223; B01J 20/28057; B01J 20/28078; B01J 20/3085; C07C 7/12; C08J 5/20; C08J 9/36; C08J 2365/00
See application file for complete search history.

(56) References Cited

U.S. PATENT DOCUMENTS

| | | |
|---|---|---|
| 8,092,581 B2 | 1/2012 | Sugiyama et al. |
| 8,203,028 B2 | 6/2012 | Kulprathipanja et al. |
| 8,313,560 B1 | 11/2012 | Cote et al. |
| 2012/0031268 A1 | 2/2012 | Yaghi et al. |

FOREIGN PATENT DOCUMENTS

| | | |
|---|---|---|
| WO | 2004002928 A1 | 1/2004 |
| WO | 2009073739 A1 | 6/2009 |
| WO | 2013144628 A1 | 10/2013 |

OTHER PUBLICATIONS

Sulfonate-Grafted Porous Polymer Networks for Preferential CO2Adsorption at Low Pressure by Weigang Lu, et al., JACS Nov. 2011.*

Conjugated Microporous Polymer Networks via Yamamoto Polymerization by Johannes Schmidt et al., Macromolecules, May 2009.*
Huang, L. et al. "Selective Adsorption of Olefin-paraffin on Diamond-like Frameworks: Diamondyne and PAF-302"; Journal of Materials Chemistry, 1(33):9433-9439 2013; abstract.
Lu, L. et al. "Sulfonate-Grafted Porous Polymer Networks for Preferential CO2 Adsorption at Low Pressure"; Journal of the American Chemical Society, 133(45):18126-18129 2011; abstract.
Lan, J. et al. "Doping of Alkali, Alkaline-Earth, and Transition Metals in Covalent-Organic Frameworks for Enhancing CO2 Capture by First-Principles Calculations and Molecular Simultations"; ACS nano, 4(7):4225-4237 2010; abstract.
Yang, Z. et al. "Effect of Li Doping on Diffusion and Separation of Hydrogen and Methane in Covalent Organic Frameworks"; The Journal of Physical Chemistry C, 116(23):12591-12598 2012; abstract.
Ben, T. et al. "Porous Aromatic Frameworks: Synthesis, Structure and Functions"; CrystEngComm., 15(1):17-26 2013; abstract.
Ma, S. et al. "Ag(I) Ion Functionalized Porous Organic Polymer as a New Platform for Highly Selective Adsorption of Ethylene over Ethane"; 2014.
Bao, Z. et al. "Adsorption of Ethane, Ethylene, Propane, and Propylene on a Magnesium-Based Metal-Organic Framework"; Langmuir, 27(22):13554-13562 2011.
Su, C. et al. "Ethene/Ethane (C2H4/C2H6) Separation through an Inorganic-Organic Hybrid Membrane Containing Silver(I) Ions as Olefin Carriers, Using Poly(N-vinylpyrrolidone) as a Mediation Agent"; Journal of the American Ceramic Society, 84(3):654-656 2001.
Augado, S. et al. "Absolute Molecular Sieve Separation of Ethylene/Ethane Mixtures with Silver Zeolite A"; Journal of the American Chemical Society, 134:14635-14637 2012.
Li, B. et al. "Introduction of n-Complexation into Porous Aromatic Framework for Highly Selective Adsorption of Ethylene over Ethane"; Journal of the American Chemical Society, 136:8654-8660 2014.
International Search Report, mailed Mar. 25, 2015.

* cited by examiner

*Primary Examiner* — Irina S Zemel
(74) *Attorney, Agent, or Firm* — Thomas | Horstemeyer, LLP

(57) ABSTRACT

Compositions containing a porous organic polymer and a monovalent metal cation are provided for separation/purification of olefins and paraffins. The compositions can be stable and recyclable. The compositions can contain acidic functional group having monovalent metal cations associated therein. The monovalent metal cations can include Ag(I) and Cu(I), capable of strong cation-pi binding to ethylene and other olefins. The compositions can have a large surface area greater than about 20 m2/g. The compositions can be used to separate/purify mixtures of ethylene and ethane. The compositions can have an ethylene/ethane adsorption selectivity of about 20 to 500 at 296 K. Methods of making the compositions are provided. Methods can include synthesizing the porous organic polymer, grafting acidic functional groups onto the polymer, and cation exchange with a salt or acid of a monovalent metal cation. Methods of olefin/paraffin separation are provided capable of achieving purities over 99%.

20 Claims, 8 Drawing Sheets

US 9,511,348 B2

FUNCTIONALIZED POROUS ORGANIC POLYMERS FOR OLEFIN/PARAFFIN SEPARATIONS

CROSS-REFERENCE TO RELATED APPLICATIONS

This application claims priority to U.S. Ser. No. 61/924,506 filed Jan. 7, 2014.

FIELD OF THE DISCLOSURE

The disclosure is generally in the field porous materials for olefin/paraffin separations.

BACKGROUND OF THE DISCLOSURE

Ethylene, one of the most widely used feedstock molecules in the petrochemical industry, is usually obtained via steam cracking and thermal decomposition of ethane. See Matar, S.; Hatch, L. F. *chemistry of petrochemical processes*, 2nd ed.; Gulf Publishing Company: Texas, 2000. The similar molecular sizes and volatilities make the separation of ethylene/ethane mixtures one of the most challenging chemical separations at large scale. See Eldridge, R. B. *Ind. Eng. Chem. Res.* 1993, 32:2208. Current technology uses cryogenic distillation performed under the condition of high pressure (23 bar) and low temperature (−25° C.), resulting in an extremely cost and energy intensive process. See Rege, S. U.; Padin, J.; Yang, R. T. *AIChE J.* 1998, 44:799. Extensive efforts to develop low energy approaches for efficient ethylene/ethane separation at higher temperature and normal atmospheric pressure have focused on membrane separation, organic solvent-based sorbents, and porous solid adsorbents. For membrane separations, see Zhu et al., *J. Am. Chem. Soc.* 2012, 134:104784. For organic solvent-based sorbents, see Safarik, et al., *Ind. Eng. Chem. Res.* 1998, 37:2571. For porous solid sorbents, see Yang, R. T. *Adsorbents: Fundamentals and Applications*; John Wiley & Sons, Inc.: New Jersey, 2003. Among these approaches, porous solid adsorbents attract particular interest because of their great potential to afford much lower cost and energy consumption.

Over the past decade, advanced porous materials such as metal-organic frameworks (MOFs) and porous organic polymers (POPs) [e.g. porous aromatic frameworks (PAFs), conjugated microporous polymers (CMPs), porous polymer networks (PPNs), porous organic frameworks (POFs)] have been explored as new classes of solid adsorbents for applications in gas storage, gas separation, carbon capture, catalysis, etc. In comparison with MOFs, POPs, despite the amorphous nature for most of them, lack preferential binding sites for ethylene molecules leading to poor ethylene/ethane adsorption selectivity.

It is an object of this disclosure to provide improved porous materials for olefin/paraffin separations.

It is an additional object of this disclosure to provide materials for olefin/paraffin separation with high olefin uptake capacities.

It is a further object of this disclosure to provide materials for olefin/paraffin separation with high selectivities for olefins.

It is also an object of this disclosure to provide methods of making improved porous materials for olefin/paraffin separations.

An object of this disclosure is also to provide methods of olefin/paraffin separation using improved porous materials.

SUMMARY

Compositions for olefin separation are provided. The compositions can contain a porous organic polymer having incorporated therein a plurality of monovalent metal cations. The porous organic polymer can be a conjugated microporous polymer, a porous aromatic framework, a porous polymer network, or a porous organic framework. For example, the porous organic polymer can be a porous aromatic framework such as cross-linked poly-tetraphenylmethane.

The compositions can be used to effectively separate olefins form paraffins, such as ethylene from ethane. The composition can have an ethylene uptake capacity of 70 cm$^3$ g$^{-1}$ to 200 cm$^3$ g$^{-1}$ at 1 atm and 296 K. The compositions can have an ethylene/ethane adsorption selectivity of 20 to 500 at 296 K. The ethylene uptake capacity can be stable and recyclable.

The compositions, including the porous organic polymer, can have a surface area from 20 m$^2$/g to 8,000 m$^2$/g. The compositions can have a pore size from 5 angstroms to 500 angstroms. The compositions can be stable, for example stable in aqueous conditions and/or stable in basic conditions.

The porous organic polymer can contain aryl moieties, such as substituted and unsubstituted benzene, naphthalene, anthracene, biphenyl, pyridine, pyrimidine, pyridazine, pyrazine and triazine. The porous organic polymer can contain acidic functional groups. In some embodiments the metal cations are associated covalently or non-covalently with the acidic functional groups. Suitable acidic functional groups can include sulfonate, phosphonate, and phosphonocarboxylate. In some embodiments, at least 50% of the acidic functional groups are associate with one of the monovalent metal cations. Suitable monovalent metal cations can include Ag(I) or Cu(I).

In some embodiments a composition for olefin separation is provided containing a cross-linked poly-tetraphenylmethane that has been grafted with sulfonate groups; and a plurality of monovalent Ag(I) cations that are associated non-covalently with the sulfonate groups.

Methods of making the compositions described herein are provided. The methods can include synthesizing a porous organic polymer; grafting acidic functional groups onto the porous organic polymer; and cation exchange with a salt of a monovalent metal cation.

Methods of separating or enriching a mixture of olefins and paraffins are provided. The methods can include passing a feedstock solution containing the olefins and paraffins, for example containing ethylene and ethane, across the composition described herein. In some embodiments, the feedstock solution contains ethylene and ethane, and the ethylene, the ethane, or both are purified to greater than 99%.

DETAILED DESCRIPTION

I. Definitions

Figure 1:
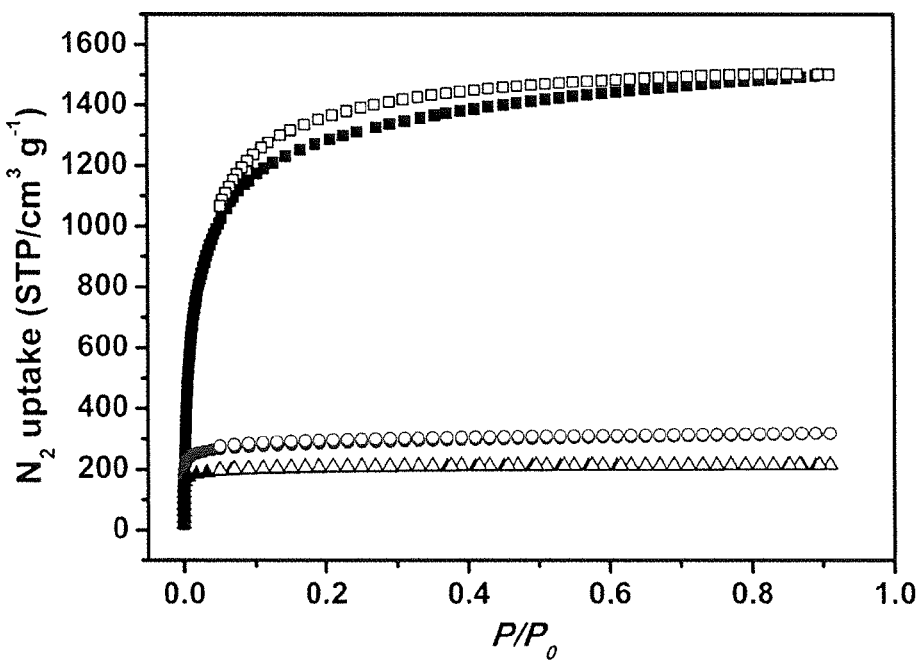
FIG. 1 is a graph of N$_2$ sorption isotherms at 77 K for cross-linked poly-tetraphenylmethane (PAF-1) (squares), sulfonate-grafted PAF-1 (PAF-1-SO$_3$H) (circles), and Ag(I) exchanged PAF-1-SO$_3$H (PAF-1-SO3Ag) (triangles). Filled: adsorption; unfilled: desorption.

The term "olefin", as used herein, refers to both substituted and unsubstituted hydrocarbons containing at least one carbon-carbon double bond. Olefins can contain from about 1 to 4 double bonds, although in some embodiments the olefin contains only 1 double bond. Olefins can have from 2 to 20, from 2 to 12, from 2 to 6, or from 2 to 4 carbon atoms. The term "olefin" can be used to refer to α-olefins or terminal olefins having a terminal double bond (as opposed to a double bond at an internal site). Exemplary olefins can include ethylene, propylene, and 1-butene.

The term "paraffin", as used herein, refers to any fully saturated hydrocarbons. Paraffins can have from 2 to 20, from 2 to 12, from 2 to 6, or from 2 to 4 carbon atoms. Paraffins can include ethane, propane, n-butane, n-pentane and the like.]

The terms "pore diameter" and "pore size", as used interchangeably herein, refer to a measure of the effective diameter of the pores in the composition. The pore diameter can be the effective diameter of the largest gas molecule that can pass through the majority of the pores in the composition. The pore diameter can be estimated from the average pore diameter obtained from crystallographic measurements. The pore diameter can be estimated from measured adsorption isotherms for an inert gas such as $N_2$ using models such as the Horvath-Kawazoe model.

The term "separation" and the corresponding verb "separate", as used herein, refer to partial of full separation of at least one component in a gaseous mixture. In a separation, at least one component may be completely removed or may be at least 99.99%, 99.9%, 99.5%, 99%, 95%, 90%, or at least 85% removed from a mixture.

The term "conjugated microporous polymer (CMP)", as used herein, refers to a class of ultrahigh surface area materials characterized by an amorphous structure made through coupling of aromatic monomers leading to extended conjugation. The extended conjugation of a conjugated microporous polymer can lead to the formation of electronic bands much like those found in conductive metals. A conjugated microporous polymer can have a surface area from about 300 m²/g to about 2,000 m²/g, about 400 m²/g to about 1500 m²/g, or about 500 m²/g to about 3000 m²/g.

The term "porous aromatic framework (PAF)", as used herein, refers to a class of ultrahigh surface area materials characterized by a rigid aromatic open-framework structure constructed by covalent bonds. Porous aromatic frameworks lack the extended conjugation found in conjugated micorporous polymers. A porous aromatic framework can have a surface area from about 500 m²/g to about 7,000 m²/g, about 1,000 m²/g to about 6,000 m²/g, or about 1,500 m²/g to about 5,000 m²/g.

The terms "porous polymer network (PPN)" and "interpenetrating polymer network (IPN)", as used interchangeably herein, refer to a class of high surface area materials containing at least two polymers, each in network form wherein at least one of the polymers is synthesized and/or crosslinked in the presence of the other. The polymer networks are physically entangled with each other and in some embodiments may be also be covalently bonded. Porous polymer networks can have a surface area from about 20 m²/g to about 6,000 m²/g, about 40 m²/g to about 500 m²/g, or about 80 m²/g to about 400 m²/g.

The terms "porous organic framework (POF)" and "covalent organic framework (COF)", as used interchangeably herein, refer to a class of highly crystalline, high surface area materials formed of small organic building blocks made entirely from light elements (H, B, C, N, and O) that are known to form strong covalent bonds. Porous organic frameworks can have a surface area from about 100 m²/g to about 5,000 m²/g, about 150 m²/g to about 4,000 m²/g, or from about 300 m²/g to about 3,000 m²/g.

The term "porous organic polymer (POP)", as used herein, refers generally to high surface area materials formed from organic segments covalently bonded to form an extended porous structure. Porous organic polymers can include conjugated microporous polymers, porous aromatic frameworks, porous polymer networks, and porous organic frameworks. The porous organic polymer can be crystalline, semi-crystalline, or amorphous. The porous organic polymer can have a surface greater than about 20 m$^2$/g, 50 m$^2$/g, 100 m$^2$/g, 500 m$^2$/g, or greater than about 1,000 m$^2$/g. The porous organic polymer can have a surface area up to about 8,000 m$^2$/g, 7,000 m$^2$/g, 6,000 m$^2$/g, 5,000 m$^2$/g, or 4,000 m$^2$/g. As used herein, the term "porous organic polymer" does not include zeolite structures or mesoporous silica structures.

The term "stable", as used herein, refers to compositions that are stable over time, stable under aqueous conditions, and/or stable under basic conditions. A composition is stable over time when, under standard operating conditions such as elevated temperatures and/or pressures, the composition does not change pore size by more than 1%, 2%, 5%, or 10% and/or does not change olefin uptake capacity by more than 1%, 2%, 5%, or 10% for a period of at least 1, 2, 10, 20, or 30 days. A composition is stable under aqueous conditions when it does not change pore size by more than 1%, 2%, 5%, or 10% and/or does not change olefin uptake capacity by more than 1%, 2%, 5%, or 10% after being exposed to an air environment with at least 60%, at least 70%, at least 80%, or at least 90% relative humidity for at least 12 hours or for at least 1, 2, 3, 4, 5, or 10 days. A composition is stable under basic conditions when it does not change pore size by more than 1%, 2%, 5%, or 10% and/or does not change olefin uptake capacity by more than 1%, 2%, 5%, or 10% after exposure to boiling 6M NaOH solution for a period of at least 120 minutes The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboam ides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

The terms "reactive coupling group" and "reactive functional group" are used interchangeably herein to refer to any chemical functional group capable of reacting with a second functional group under the given conditions to form a covalent bond. Those skilled in the art will recognize that some functional groups may react under certain conditions but not under others. Accordingly, some functional groups may be reactive coupling groups only certain conditions, e.g. under conditions where the groups react to form a covalent bond. The selection of reactive coupling groups is within the ability of the skilled artisan. Examples of reactive coupling groups can include primary amines (—NH$_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. Examples of reactive coupling groups can include click reactive coupling groups capable of forming covalent bonds through click reactions. Well-known reactions include the hetero-Diels-Alder reaction, the thiol-ene coupling, the Staudinger ligation, native chemical ligation, and the amidation reaction between thio acids or thio esters and sulfonyl azides (refered to as 'sulfo-click'). As used herein, the terms "sulfo-click" and "sulfo-click chemistry" are used to refer to a reaction between thio acids and sulfonyl azides containing molecules, creating a covalent bonds between the two molecules. Examples of sulfo-click chemistry are described in U.S. Patent Application Publication 2011/0130568 and PCT Publication WO 2012/021486. The coupling reaction may include the use of a catalyst, heat, pH buffers, light, or a combination thereof.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, and $C_3$-$C_{30}$ for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

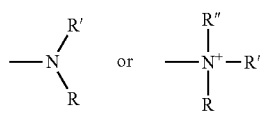

wherein R, R', and R" each independently represent a hydrogen, an alkyl, an alkenyl, —(CH2)$_m$-$R_C$ or R and R' taken together with the N atom to which they are attached complete a heterocycle having from 4 to 8 atoms in the ring structure; $R_C$ represents an aryl, a cycloalkyl, a cycloalkenyl, a heterocycle or a polycycle; and m is zero or an integer in the range of 1 to 8. In preferred embodiments, only one of R or R' can be a carbonyl, e.g., R, R' and the nitrogen together do not form an imide. In still more preferred embodiments, the term "amine" does not encompass amides, e.g., wherein one of R and R' represents a carbonyl. In even more preferred embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group The term "amido" is art-recognized as an amino-substituted carbonyl and includes a moiety that can be represented by the general formula:

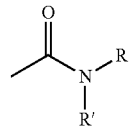

wherein R and R' are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H, 6H-1, 5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle", as used herein, refers to an aromatic or non-aromatic ring(s) in which each atom of the ring(s) is carbon.

"Heterocycle" or "heterocyclic", as used herein, refers to a monocyclic or bicyclic structure containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

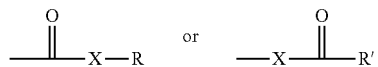

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid". Where X is an oxygen and R' is hydrogen, the formula represents a "formate". In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic As used herein, the term "nitro" means —$NO_2$; the term "halogen" designates —F, —Cl, —Br, or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

II. Compositions for Olefin Separation

Compositions for olefin separation are provided. The compositions contain a porous organic polymer having incorporated therein a plurality of monovalent metal cations. The compositions can be stable. For example, the compositions can be stable under aqueous conditions, stable under basic conditions, stable under high pressure, or a combination thereof. The compositions can be useful for the separation of olefins (e.g. ethylene, propylene, etc.) from paraffins (e.g. ethane, propane, etc.). There are many porous organic polymers and many monovalent cations that may be used. In some embodiments the porous organic polymer is a porous aromatic framework, and the monovalent metal cations are Ag(I) or Cu(I) cations. For example, the composition can be a cross-linked poly-tetraphenylmethane having Ag(I) cations incorporated therein.

The compositions can contain a porous organic polymer. Porous organic polymers provide a high surface area and range of pore sizes that can be useful for olefin separation. The porous organic polymer can be a conjugated microporous polymer, a porous aromatic framework, a porous polymer network, or a porous organic framework. The porous organic polymer can be crystalline, semi-crystalline, or amorphous. The porous organic polymer can be stable. For example, the porous organic polymer can be stable under aqueous conditions, stable under basic conditions, stable under high pressure, or a combination thereof.

The porous organic polymer can be a conjugated microporous polymer, a porous aromatic framework, a porous polymer network, a porous organic framework, or a mesoporous organic polymer. Suitable porous polymers can include fluoropolymers, e.g. polytetrafluoroethylene or polyvinylidene fluorides, polyolefins, e.g. polyethylene or polypropylene; polyamides; polyesters; polysulfone, poly(ethersulfone) and combinations thereof, polycarbonate, polyurethanes. Suitable porous aromatic frameworks can include cross-linked poly-tetraphenylmethane, poly-teraphenyl silane, and poly-triphenyl amine polymers.

The porous organic polymer can have any surface are useful for the particular olefins to be separated. In some embodiments the porous organic polymer will have a surface area greater than about 20 m²/g, greater than about 50 m²/g, greater than about 100 m²/g, greater than about 200 m²/g, greater than about 300 m²/g, greater than about 400 m²/g, greater than about 500 m²/g, greater than about 600 m²/g, greater than about 700 m²/g, greater than about 800 m²/g, or greater than about 1,000 m²/g. For example, the porous organic polymer can have a surface area from about 20 m²/g to about 8,000 m²/g, from about 40 m²/g to about 7,000 m²/g, from about 60 m²/g to about 6,000 m²/g, from about 100 m²/g to about 5,000 m²/g, from about 400 m²/g to about 5,000 m²/g, from about 400 m²/g to about 4,000 m²/g, from about 400 m²/g to about 2,000 m²/g, or from about 500 m²/g to about 1,500 m²/g.

The porous organic polymer can have a range of pore sizes. For example, the pore size can be adjusted to best accommodate the particular olefins/paraffins to be separated. The porous organic polymer can have a pore size from about 5 Å to about 2,000 Å, from about 5 Å to about 1,500 Å, from about 5 Å to about 1,000 Å, from about 5 Å to about 500 Å. In some embodiments a composition useful for the separation of ethylene from ethane can have a pore size of about 2 Å to about 20 Å, from about 2 Å to about 15 Å, from about 5 Å to about 15 Å, from about 5 Å to about 10 Å, or about 8 Å.

The porous organic polymer can contain monomer units having an aryl moiety. A variety of porous organic polymers can be made with aryl moieties. For example, the porous organic polymer can contain a monomer unit containing an aryl moiety selected from the group consisting of substituted and unsubstituted benzene, naphthalene, anthracene, biphenyl, pyridine, pyrimidine, pyridazine, pyrazine and triazine.

The porous organic polymer can contain one or more acidic functional groups. Acidic functional groups can provide ion exchange sites for coordinating the monovalent metal cations. For example, a sulfonic acid group can under ion exchange to form the corresponding metal sulfonate complex:

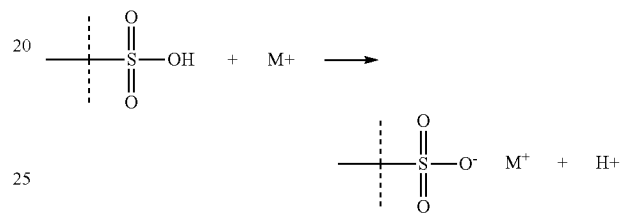

In some embodiments the acidic functional group can be a sulfonic acid group, a phosphonic acid group, or a carboxylic acid group.

In some embodiments the porous organic polymer contains a monomer unit selected from

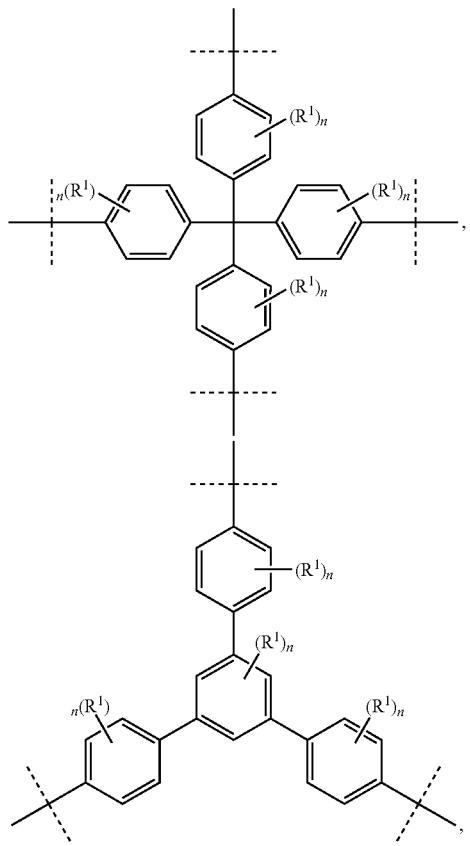

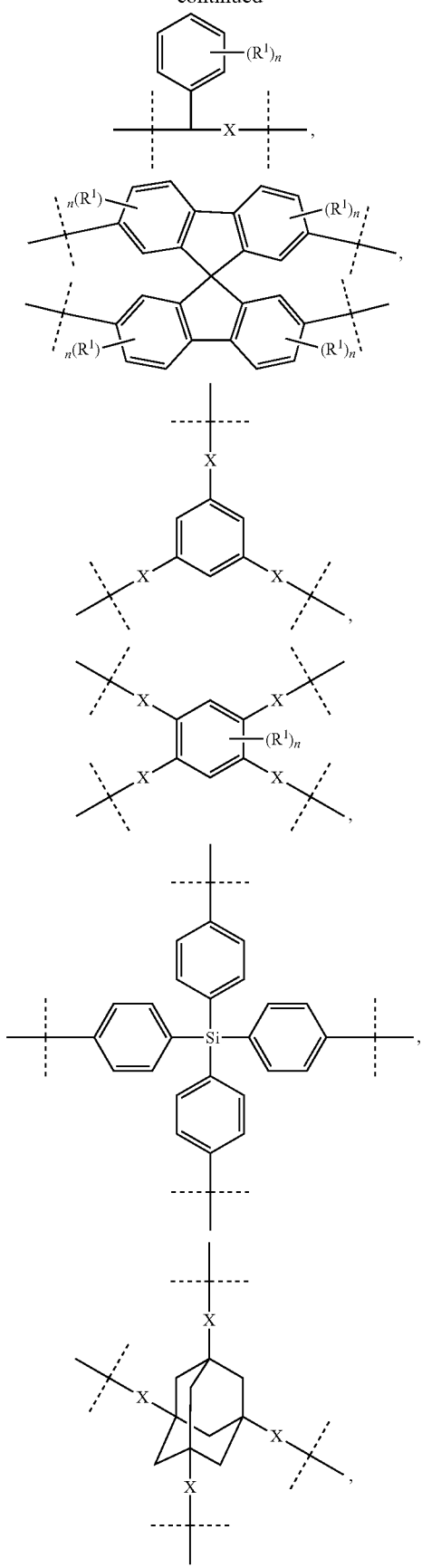

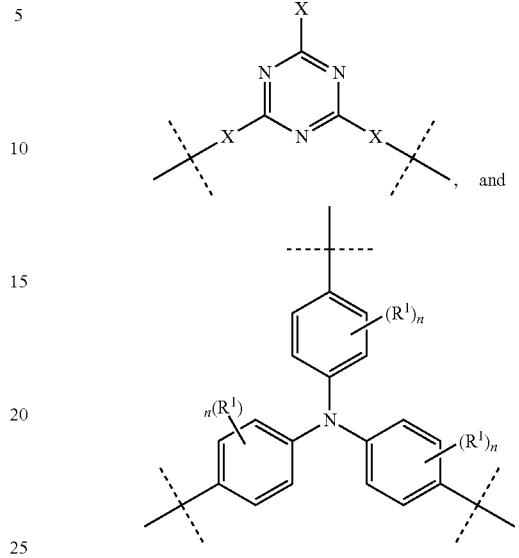

wherein each occurrence of X is independently selected from —$CH_2$—, phenylene, and ═, optionally containing one or more $R^1$ substituents; wherein each occurrence of $R^1$ is independently selected from substituted and unsubstituted alkyl, heteroalkyl, alkylthio, alkoxy, amino, and acidic functional groups having from 1 to 20, from 1 to 12, from 1 to 10, or from 1 to 5 carbon atoms; wherein each occurrence of n is an integer 1, 2, 3, or 4. In some embodiments, the porous organic polymer contains monomer units having at least one, at least two, at least three, or at least four acidic functional groups per monomer unit. Suitable acidic functional groups can include sulfonic acid groups, phosphonic acid groups, and carboxylic acid groups.

The compositions can contain a plurality of monovalent metal cations incorporated within the porous organic polymer. Monovalent metal cations can include alkali metals such as Li, Na, K, Rb, and Cs and monovalent Ag(I) and Cu(I). The monovalent metal cation can be associated covalently or noncovalently with the porous organic polymer. For example, the monovalent metal cation can be associated with the porous organic polymer through electrostatic Coulomb interactions and/or through cation-pi interactions. In some embodiments the monovalent metal cation is associated with an acidic functional group (or the negatively charged conjugate base thereof) on the porous organic polymer through strong electrostatic interactions. The monovalent metal cations can form strong cation-pi interactions with olefins, leading to strong binding of olefins, improved olefin adsorption, and/or improved olefin/paraffin adsorption selectivity.

The compositions can have large olefin uptake capacities, large olefin/paraffin selectivities, and/or strong olefin binding energies. The compositions can have an olefin uptake capacity at 1 atm and 296 K of about 40 $cm^3$ $g^{-1}$ to 1,000 $cm^3$ $g^{-1}$, about 50 $cm^3$ $g^{-1}$ to 800 $cm^3$ $g^{-1}$, about 60 $cm^3$ $g^{-1}$ to 600 $cm^3$ $g^{-1}$, about 60 $cm^3$ $g^{-1}$ to 400 $cm^3$ $g^{-1}$, about 70 $cm^3$ $g^{-1}$ to 300 $cm^3$ $g^{-1}$, about 70 $cm^3$ $g^{-1}$ to 200 $cm^3$ $g^{-1}$, or about 80 $cm^3$ $g^{-1}$ to 150 $cm^3$ $g^{-1}$ The compositions can have an olefin/paraffin selectivity at 296K of about 10 to 1,000, about 10 to 900, about 20 to 800, about 20 to 600, about 20 to 500, about 30 to 400, about 40 to 400, or about 50 to 300.

The compositions can have olefin isoteric heats of adsorption of about 20 kj mol$^{-1}$ to 250 kJ mol$^{-1}$, about 40 kj mol$^{-1}$ to 250 kJ mol$^{-1}$, about 40 kj mol$^{-1}$ to 200 kJ mol$^{-1}$, about 50 kj mol$^{-1}$ to 150 kJ mol$^{-1}$, or about 80 kj mol$^{-1}$ to 100 kJ mol$^{-1}$. In some embodiments, the olefin is ethylene and the compositions have an ethylene uptake capacity of about of about 70 cm$^3$ g$^{-1}$ to 300 cm$^3$ g$^{-1}$ or about 70 cm$^3$ g$^{-1}$ to 200 cm$^3$ g$^{-1}$; the composition have an ethylene/ethane selectivity at 296K of about 20 to 600 or about 20 to 500; and the compositions have an ethylene isoteric heat of adsorption of about 50 kj mol$^{-1}$ to 150 kJ mol$^{-1}$ or about 80 kj mol$^{-1}$ to 100 kJ mol$^{-1}$.

The monovalent metal cations can form strong cation-pi interactions with olefins, leading to strong binding of olefins, improved olefin adsorption, and/or improved olefin/paraffin adsorption selectivity. In some embodiments, the compositions have an olefin uptake efficiency that is at least 50% more, 70% more, 80% more, 90% more, or at least 100% more than the olefin uptake efficiency of the corresponding composition without the monovalent metal cations when measured under the same conditions except where the monovalent metal cations have been replaced by hydrogen cations. In some embodiments, the compositions have an olefin/paraffin selectivity that is at least 2, 3, 5, 10, or 20 timed the olefin/paraffin selectivity of the corresponding composition without the monovalent metal cations when measured under the same conditions except where the monovalent metal cations have been replaced by hydrogen cations.

III. Methods of Making Compositions for Olefin Separation

Methods of making compositions for olefin separation are provided. The methods can include making any of the compositions described above or below. The methods can include (1) synthesizing a porous organic polymer (2) ion exchange with a salt of a monovalent metal cation to incorporate the monovalent metal cations into the porous organic polymer. The methods can include functionalizing the porous organic polymer with an acidic functional group prior to the ion exchange step, for example by grafting with a sulfonate moiety.

Methods of synthesizing porous organic polymers are known and described, for example, in U.S. Pat. No. 8,470, 900; Chakraborty et al., *Chem. Sci.*, 2015, 6:384-389; Zhao et al., *Chem. Commun.*, 2013, 49:2780-2782; Wang et al., *Dalton Trans.*, 2012, 41:3933-3936. In some embodiments porous organic polymers are synthesized according to methods described in Lu et al., *J. Am. Chem. Soc.* 2011, 133: 18126 or slight modifications thereof.

Methods of grafting acidic groups onto polymers are known. For example, the methods can include sulfonation with sulfonic acid or a chlorosulfonic acid to yield the corresponding sulfonic acid functionalized polymer. In some embodiments, sulfonation is performed by mixing the polymer with approximately one molar equivalent of chlorosulfonic acid in a solvent such as dichlormethane or nitromethane. The reaction can be performed at temperatures of about −15° C. to 40° C., about −5° C. to 35° C., or about 5° C. to 30° C.

Methods of cation exchange can include partial or full replacement of the acidic protons in the porous organic polymer with a monovalent metal cation. In some embodiments, more than 20%, 30%, 40%, 50%, 60%, or more than 80% of the acidic protons are replaced with monovalent metal cations by cation exchange. The monovalent metal cations are generally added to the porous organic polymer in the form of a salt or an acid. The anionic counterion associated with the metal is not specifically defined, provided that is does not adversely affect the modification (i.e. cation exchange) reactions. Suitable anions include but are not limited to acetate, carboxylate, benzoate, bromate, chlorate, perchlorate, chorite, citrate, nitrate, nitrite, sulfates, and halide (F, Cl, Br, I) and mixtures thereof. Suitable acids include inorganic and organic acids, with inorganic acids being preferred. The porous organic polymer may be cation exchanged by any of the known conventional techniques. For example, a porous organic polymer may be cation exchanged by treatment with a salt or acid of a monovalent metal cation in a stirred aqueous solution. After the cation exchange reactions are carried out, the resulting modified porous organic polymer can be treated in any conventional manner, including but not limiting to washing and drying steps.

IV. Methods of Olefin Separation

Methods of olefin/paraffin separation are provided. The methods can include using any of the compositions described herein with any cycle swing adsorption process for the separation/enrichment of binary or multi-component mixtures of olefins and paraffins. For example, pressure swing adsorption (PSA) processes including vacuum swing adsorption (VSA), thermal swing adsorption (TSA) processes and combinations thereof can be used. The cycle swing adsorption process can include multiple adsorption and regeneration steps as well as purging and depressurization steps. Pressure swing and temperature swing processes are well known in the art. In some embodiments, the olefin, the paraffin, or both can be purified to greater than 90%, 95%, 99%, 99.9%, or greater than 99.95% using the methods provided herein. In some embodiments the olefin is ethylene and the paraffin is ethane.

Pressure swing adsorption (PSA) processes generally include i) a high pressure adsorption step, during which a component in a gaseous mixture is selectively adsorbed onto an adsorbent substrate ii) a purging step, during which non-adsorbed components are collected as waste, recycle or product effluent; and iii) a low pressure de-sorption step or regeneration step, during which the selectively adsorbed component is released form the adsorbent substrate (see for example, U.S. Pat. No. 6,197,092 that is incorporated herein by reference). Pressure swing adsorption can include, in addition to adsorption and regeneration steps: purge steps, venting steps, pressure equalization steps, evacuation steps, blow-down steps. Steps can be carried out in concurrent, alternating or sequential fashion and gas flows can be continuous, discontinuous, co-current and counter-current, all of which are well known in the art. In a PSA process one or more adsorbent beds can be arranged in series or in parallel. Some non-limiting examples of PSA processes are described in Adsorption, Gas Separation in the Kirk-Othmer Encyclopedia of Chemical Technology, Copyright John Wiley & Sons, Inc. vol 1, pgs 642-647 and references cited therein as well as in U.S. Pat. Nos. 3,430,418; 4,589,888; 6,293,999; 6,197,092 and 6,497,750 all of which are incorporated herein by reference. In a PSA processes, the adsorbent material is typically packed in one or more beds, and various pressurization/depressurization protocols including the application of vacuum can be used (see Adsorption, Gas Separation in the Kirk-Othmer Encyclopedia of Chemical Technology, Copyright John Wiley & Sons, Inc. vol 1, pg 617 and references cited therein).

Temperature swing adsorption (TSA) is described in Adsorption, Gas Separation in the Kirk-Othmer Encyclopedia of Chemical Technology, Copyright John Wiley & Sons, Inc. vol 1, pgs 636-642 and references cited therein all of which are incorporated herein by reference.

In some embodiments, at least one adsorbent bed containing any one of the compositions described herein is used in a pressure swing adsorption process to separate/enrich gaseous mixtures of olefins and paraffins having the same number of carbon atoms, preferably for the separation of ethylene from, or the enrichment of ethylene within, a gaseous mixture containing ethylene and ethane. In some embodiments the pressure swing adsorption process is carried out at room temperature or at a temperature of about 0° to about 50° C., about 5° to about 40° C., about 10° to about 40° C., about 10° to about 30° C., about 15° to about 30° C., about 20° to about 30° C., or about 23° to about 26° C. In some embodiments the pressure swing adsorption process is a combined pressure swing/temperature swing adsorption process.

The pressures at which adsorption and regeneration steps are carried out are not specifically defined, and depend on a number of factors such as but not limited to the temperature used, the type of cation used to modify the porous organic polymer, and the nature of the olefin and paraffin to be separated/enriched. Typically, the range of absolute pressures used during the adsorption step can be from about 10 kPa to about 2,000 kPa, from about 50 kPa to about 1000 kPa. The range of pressures used during the release of adsorbate (i.e. during the regeneration step) can be from about 0.01 kPa to about 150 kPa, or from about 0.1 kPa to about 50 kPa.

The temperatures at which the adsorption over the modified ETS-10 zeolite takes place will depend on a number of factors, such as but not limited to the particular olefin and paraffin to be separated/enriched, the type of cation used to modify the porous organic polymer, and the pressure at which adsorption is to be carried out. In general, the adsorption step can be carried out at from ambient temperatures to above about 100° C., provided that the temperatures do not exceed temperatures at which chemical reaction of the olefin, such as a polymerization reaction, takes place. Temperatures that favor adsorption and desorption over the pressure range of about 0.1 kPa to about 1000 kPa are generally preferred. For reasons of economics, in some embodiments, it is desirable to use ambient temperatures during both the adsorption and desorption steps.

In some embodiments, a porous organic polymer composition provided herein is used to selectively adsorb ethylene from a gaseous feedstream containing ethylene and ethane, to produce an adsorbed phase enriched in ethylene and a non-adsorbed phase enriched in ethane. Desorption from the porous organic polymer occurs at a pressure which is lower than the adsorption pressure, and a gaseous mixture rich in ethylene is recovered as product or may be further enriched by further treatment with porous organic polymer. The feedstream may optionally contain gases such as carbon monoxide, carbon dioxide and hydrogen. Components such as hydrogen sulfide may also be present in the feedstream. In some embodiments, these optional components are removed prior to contact of the feedstream with the porous organic polymer. Methods to remove hydrogen, hydrogen sulfide, carbon monoxide etc. are well known in the art.

The porous organic polymer can be used in a pressure swing adsorption (PSA) process that receives product feedstreams from a hydrocarbons cracking unit or plant. A hydrocarbon cracking unit typically employs hydrothermal pyrolysis or high temperature catalytic processes to crack feedstocks such as but not limited to natural gas, naphtha and gas oil, for the production of light olefins such as ethylene and propylene.

The methods and processes of can be used in a variety of petroleum refining and petrochemical operations where the separation of ethylene/ethane product streams is desired. For example, the current process can be used to perform a rough separation of ethylene and ethane prior to cryogenic fractionation of ethylene and ethane or alternatively to perform a final purification or finishing step after a rough cut distillative separation of ethylene and ethane. Cryogenic fractionation of ethylene from ethane is well known in the art. The generation of a C2 feedstream from the products of hydrocracking is also well known in the art and principally involves compression, acetylene hydrogenation, de-methanization, and various fractionation steps to remove higher olefins and higher paraffins.

The porous organic polymer can be used in one or more PSA beds, upstream of a ethylene/ethane distillation unit (i.e. a C2 splitter column). Alternatively, one or more PSA beds containing porous organic polymer can be downstream of an ethylene/ethane distillation unit.

EXAMPLES

Materials, Syntheses, and Characterization. All starting materials, reagents, and solvents were purchased from commercial sources (Aldrich, Alfa, Fisher, and Acros) and used with-out further purification.

Elemental analyses were performed on a Perkin-Elmer 2400 element analyzer. Inductively coupled plasma (ICP) analysis was performed on a Perking-Elmer Optima 3300DV spectrometer. IR spectra were recorded on a Nicolet Impact 410 FTIR spectrometer. XPS measurements were performed on an ESCALAB 250 X-ray photoelectron spectroscopy, using Mg Kα X-ray as the excitation source. Thermogravimetric analysis (TGA) was performed under nitrogen on a TA Instrument TGA 2950 Hi-Res. $^{13}$C NMR were performed on a Bruker AVANCE IIIHD console with 1.9 mm MAS probe. DSC analysis was performed on a TA Q20 analyzer, the ramping rate is 2° C./min.

Gas sorption measurements were performed using an ASAP 2020 volumetric adsorption analyzer. High-purity grade gases of $N_2$ (99.999%), $C_2H_4$ (99.5%), and $C_2H_6$ (99.5%) were used for the collection of respective sorption isotherms.

In situ IR experiments. IR spectra of ethylene adsorption were collected using a Thermo Nicolet Nexus 670 spectrometer in diffuse reflectance mode (DRIFTS). The PAF-1-$SO_3$Ag sample, ca. 5 mg, was treated in a DRIFTS cell (HC-900, Pike Technologies) at 423 K in helium (30 mL/min) for 1 hour to removal water and other adsorbates. The sample was then cooled down to room temperature for ethylene adsorption. The adsorption was conducted by flowing 10% ethylene/He (30 mL/min) over the sample for 5 min and then desorption was done in flowing helium. IR spectra were recorded continuously to follow the surface changes during the adsorption and desorption process. All reported IR spectra are difference spectra referenced to a background spectrum collected at room temperature after pre-treatment but prior to ethylene adsorption.

Example 1

Materials Preparation and Physicochemical Characterization

PAF-1 [(cross-linked poly-tetraphenylmethane) also known as (a.k.a.) PPN-6] is an amorphous POP possessing a hypothetical diamondoid-topology structure with very high surface area, and exceptional stability in water/moisture and acidic/basic media. PAF-1-SO$_3$Ag can be readily achieved by Ag(I) ion exchange of sulfonate-grafted PAF-1 (hereafter denoted PAF-1-SO$_3$H) following procedures reported herein.

Scheme 1. Synthetic route of PAF-1-SO$_3$Ag.

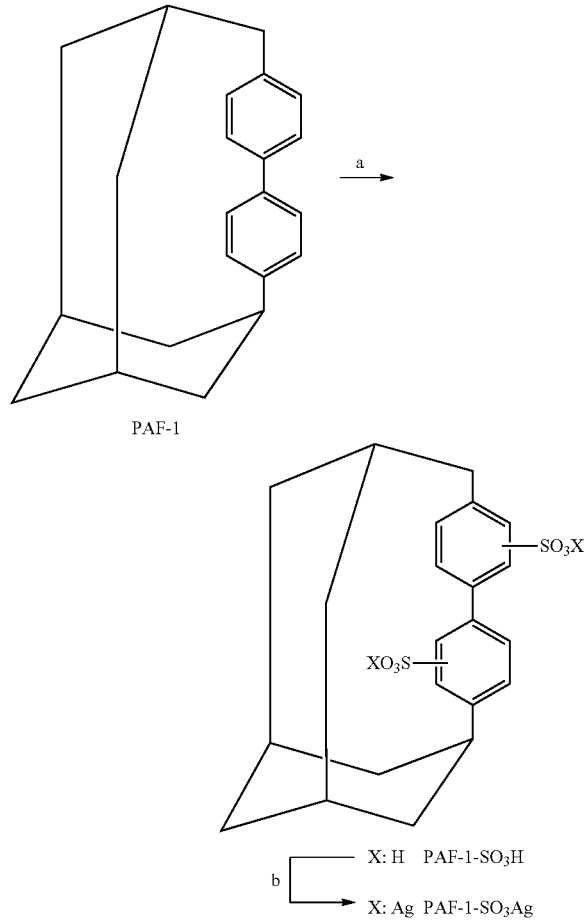

(a) CH$_2$Cl$_2$, ClSO$_3$H, 25° C., 3 days; (b) AgNO$_3$, CH$_3$CN/H$_2$O, 3 times.

Synthesis of tetrakis(4-bromophenyl)methane. To a three-necked round-bottom flask containing bromine (6.4 mL, 19.9 g), tetraphenylmethane (2.0 g, 6.24 mmol) was added step-wise with small portions under vigorous stirring at room temperature (25° C.). After the addition was completed, the resulting solution was stirred for 60 min and then cooled to 0° C. At 0° C. temperature, ethanol (25 mL) was added slowly and the reaction mixture was allowed to warm to room temperature overnight. Then, the precipitate was filtered off and washed subsequently with saturated aqueous sodium hydrogensulfite solution (25 mL) and water (100 mL). After drying at 80° C. for 24 h under vacuum (80 mbar), tetrakis(4-bromophenyl) methane was recrystallized in EtOH/CH$_2$Cl$_2$ to afford a yellow solid, yield: 88%.

Synthesis of PAF-1. Tetrakis(4-bromophenyl)methane (509 mg, 0.8 mmol) was added to a solution of 2,2'-bipyridyl (565 mg, 3.65 mmol), bis(1,5-cyclooctadiene)nickel(0) (1.0 g, 3.65 mmol), and 1,5-cyclooctadiene (0.45 mL, 3.65 mmol) in anhydrous DMF/THF (60 mL/90 mL), and the mixture was stirred overnight at room temperature under nitrogen atmosphere. After the reaction, 6 M HCl (60 mL) was added slowly, and the resulting mixture was stirred for 12 h. The precipitate was collected by filtration, then washed with methanol and water, and dried at 150° C. for 24 h under vacuum (80 mbar) to produce PAF-1 as a white powder, yield: 80%.

Synthesis of PAF-1-SO$_3$H. To an ice-cooled mixture of PAF-1 (100 mg) in dichloromethane (15 mL), chlorosulfonic acid (1.0 mL) was added drop wise. The resulting mixture was stirred at room temperature for three days. Then, the mixture was poured into ice, and the solid was collected, washed with water thoroughly, and dried 150° C. for 24 h under vacuum (80 mbar) to produce PAF-1-SO$_3$H as blue powder, yield: 96%.

Synthesis of PAF-1-SO$_3$Ag. To the 15 ml CH$_3$CN/H$_2$O (1:1) solution, 100 mg PAF-1-SO$_3$H and 800 mg AgBF$_4$ were added. The mixture was stirred under room temperature for 48 h, and then the solid was collected by filtration followed by washing with CH$_3$CN and water. The whole process was performed carefully under dark environment. This exchange process was repeated for three times, and then dried at 110° C. under vacuum (80 mbar) for further test, yield: 94%. EA: C: 47.25%; H: 3.19%; N: 0.53%; S: 17.11%; ICP-MS: Ag: 29.20%.

Figure 2:
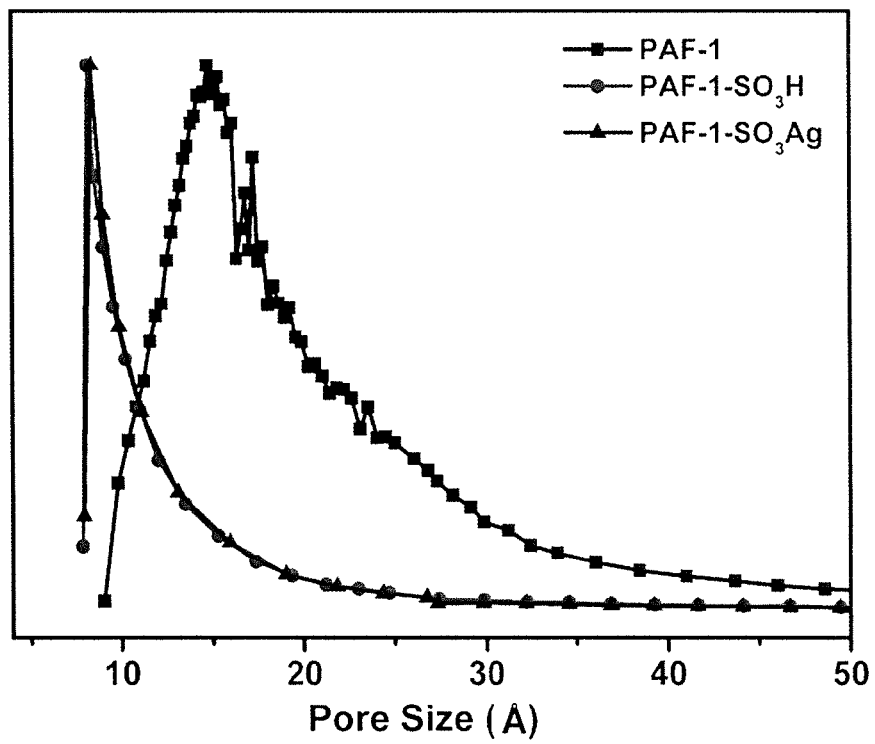
FIG. 2 is a graph of the pore size distribution of cross-linked poly-tetraphenylmethane (PAF-1) (squares), sulfonate-grafted PAF-1 (PAF-1-SO$_3$H) (circles), and Ag(I) exchanged PAF-1-SO$_3$H (PAF-1-SO3Ag) (triangles) determined using the Horvath-Kawazoe model.
Figure 3:
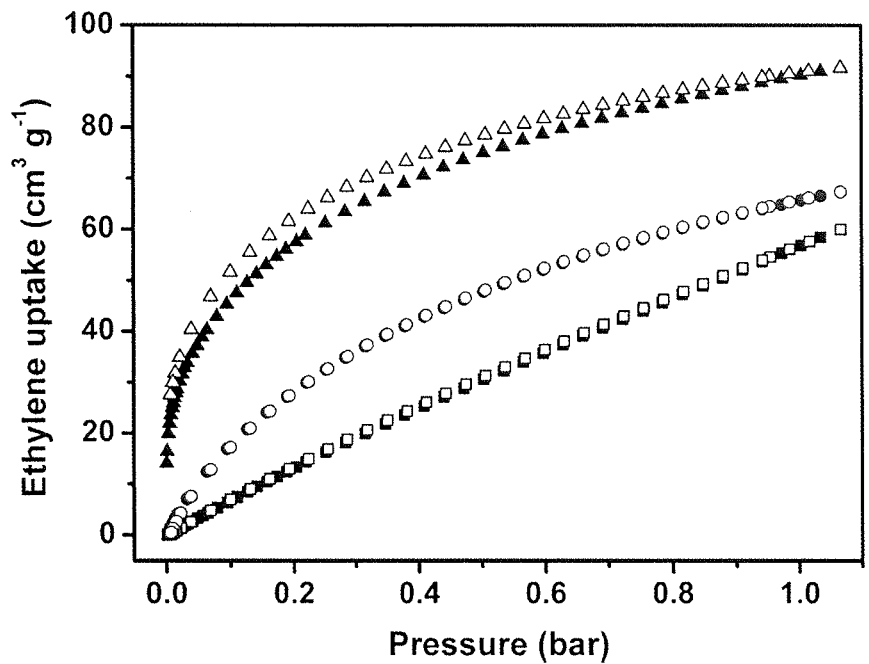
FIG. 3 is a graph of ethylene sorption isotherms of cross-linked poly-tetraphenylmethane (PAF-1) (squares), sulfonate-grafted PAF-1 (PAF-1-SO₃H) (circles), and Ag(I) exchanged PAF-1-SO₃H (PAF-1-SO3Ag) (triangles) at 296 K. Filled: adsorption; unfilled: desorption.

Characterization. N$_2$ gas sorption isotherms at 77 K (FIG. 1) reveal Brunauer Emmett Teller (BET) surface areas of 4714 m$^2$·g-1, 1087 m$^2$·g-1, and 783 m$^2$·g-1 for PAF-1, PAF-1-SO$_3$H, and PAF-1-SO$_3$Ag, respectively. Pore size distribution analysis (Horvath-Kawazoe model) indicates that the pore size is reduced from ~15 Å for PAF-1 to ~8 Å for PAF-1-SO$_3$H, whereas the pore size of PAF-1-SO$_3$Ag is predominantly distributed around ~8 Å suggesting negligible pore size change after the Ag(I) ion exchange process (FIG. 2).

The presence of Ag(I) in PAF-1-SO$_3$Ag was confirmed by X-ray photoelectron spectroscopy (XPS) analysis, which shows silver signal at binding energy of 368.8 eV and 374.8 eV corresponding to the peaks of Ag3d$_{5/2}$ and Ag3d$_{3/2}$, respectively. Fourier transform infra-red spectroscopy (FTIR) of PAF-1-SO$_3$Ag shows the obvious characteristic peak of SO$_3$-group at 1086 cm$^{-1}$ and 1186 cm$^{-1}$, respectively. Solid $^{13}$C NMR spectra of PAF-1-SO$_3$Ag and PAF-1-SO$_3$H show similar central carbon atom signals at δ=65 ppm and the signals of aromatic carbon (δ=121 ppm to 147 ppm), indicating the preservation of framework structure after Ag(I) ion exchange. Inductively coupled plasma mass spectrometry (ICP-MS) and elemental analysis (EA) indicate that ~50% SO$_3$H were exchanged into SO3Ag.

Example 2

Ethylene and Ethane Adsorption

Figure 4:
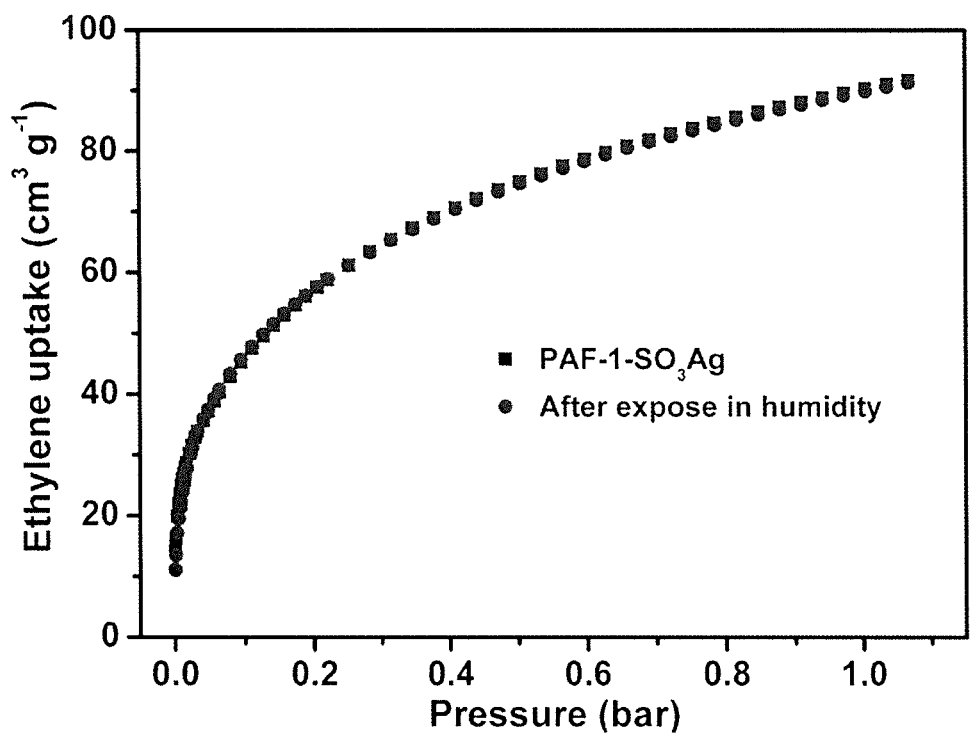
FIG. 4 is a graph of ethylene adsorption isotherms of Ag(I) exchanged sulfonate-grafted cross-linked poly-tetraphenylmethane (PAF-1-SO₃Ag) both before (squares) and after (circles) being exposed to humidity (80%) for two days followed by activation at 105° C.
Figure 7:
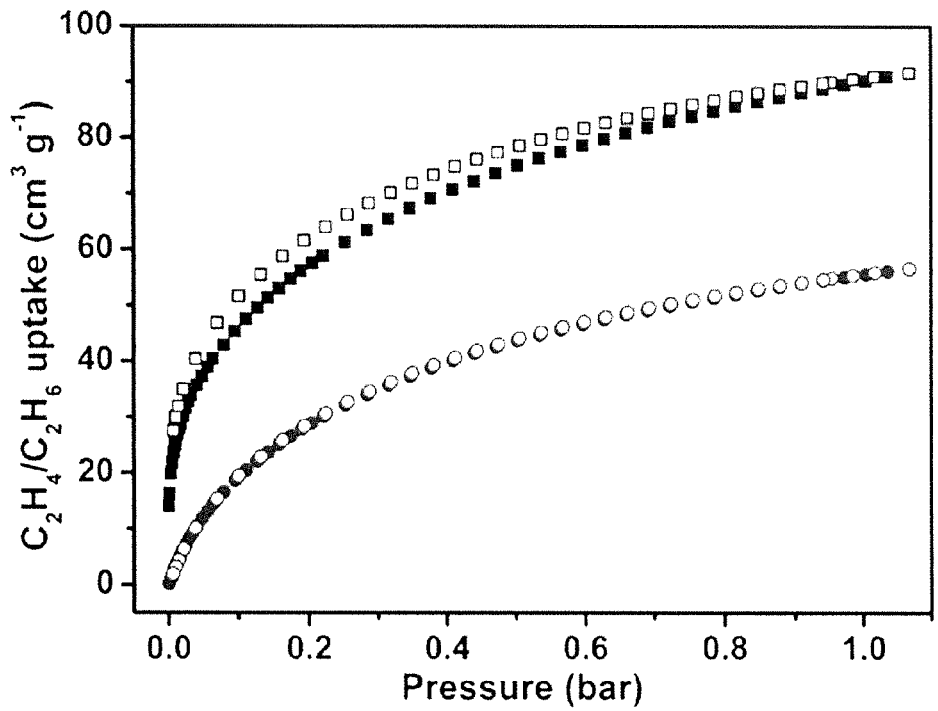
FIG. 7 is a graph of $C_2H_4$ (squares) and $C_2H_6$ (circles) sorption isotherms for Ag(I) exchanged sulfonate-grafted cross-linked poly-tetraphenylmethane (PAF-1-SO₃Ag) at 296 K. Filled: adsorption; unfilled: desorption.

The low-pressure ethylene sorption isotherms were collected at 296 K. The incorporation of Ag(I) ion into PAF-1 results in a significant enhancement of ethylene adsorption capacity despite the remarkable decrease in surface area. At 296 K and 1 atm, the ethylene uptake amounts of PAF-1 and PAF-1-SO$_3$H are 57 cm$^3$·g$^{-1}$ and 66 cm$^3$·g$^{-1}$, respectively. In contrast, PAF-1-SO$_3$Ag exhibits a significantly higher ethylene uptake capacity of 91 cm$^3$·g$^{-1}$ (4.1 mmol·g$^{-1}$) under the same conditions (FIG. 7). PAF-1-SO$_3$Ag surpasses the ethylene uptake capacity of zeolite 5 Å (Mofarahi et al., Adsorption 2013, 19:101.) (~2.3 mmol·g$^{-1}$ at 303 K and 1 atm) and compares to that of zeolite NaX (Choudhary, et al., J. Chem. Soc. Faraday Trans. 1995, 91:2935.) (~4.2 mmol·g$^{-1}$ at 305 K and 1 atm), two benchmark zeolites widely studied for ethylene/ethane separation. In addition, PAF-1-SO$_3$Ag out-performs the copper(catecholate) decorated POP, CuA$_{10}$B$_1$, in ethylene uptake, which exhibits an ethylene adsorption amount of ~1.8 mmol·g-1 at 0.79 atm and 298 K. Weston et al., *J. Mater. Chem. A* 2014, 2:299. The ethylene uptake capacity of PAF-1-SO$_3$Ag at 296 K and 1 atm is relatively lower compared to that of some high surface area MOFs possessing open metal sites (e.g. 7.2 mmol·g$^{-1}$ of MgMOF-74, 7.2 mmol·g$^{-1}$ of Cu-BTC, and 5.8 mmol·g$^{-1}$ of NOTT-102), but the MOFs containing open metal sites usually experience partial framework degradation after exposed to moisture, inevitably leading to drastic decreases in ethylene uptake capacity upon reuse. In contrast, the fact that PAF-1-SO$_3$Ag was prepared via ion exchange in aqueous solution suggests its water stability. This together with its moisture stability is further confirmed by the reproducibility of the ethylene sorption isotherms for PAF-1-SO$_3$Ag even after exposure to an air environment with 80% humidity for two days (FIG. 4).

Figure 5:
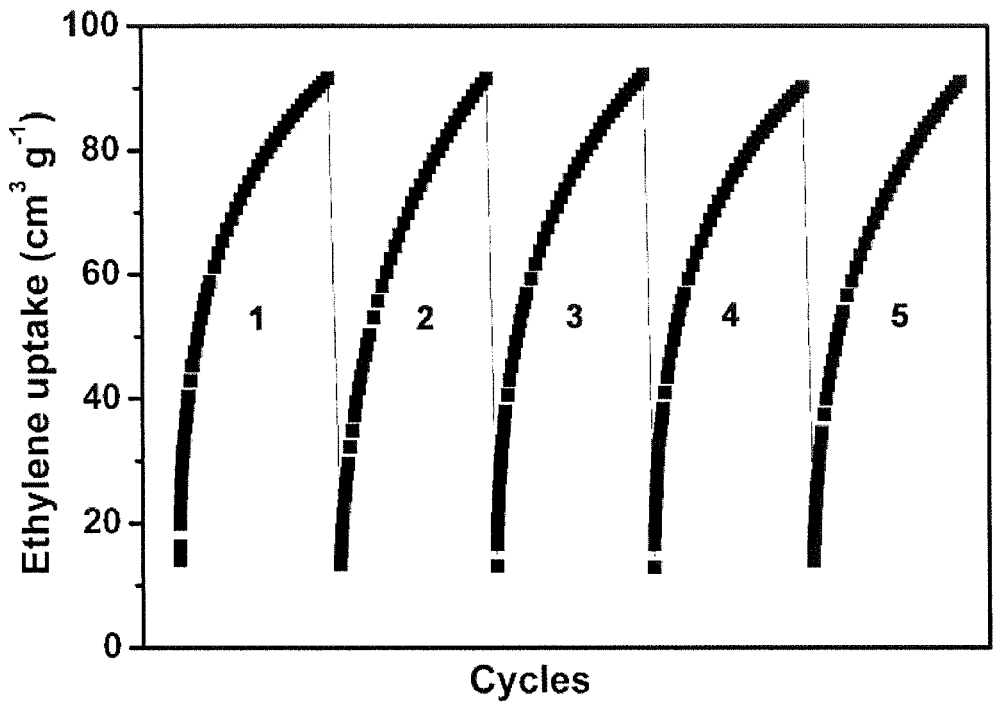
FIG. 5 is a graph of five cycles of ethylene uptake for Ag(I) exchanged sulfonate-grafted cross-linked poly-tetraphenylmethane (PAF-1-SO₃Ag) at 296 K.

To test the recyclability of PAF-1-SO$_3$Ag, temperature and vacuum swings were simulated with an ASAP2020 analyzer, by saturating with ethylene up to 1.1 bar at 296 K followed by a high vacuum for 3 h at 105° C. After 5 cycles, there was no apparent loss in capacity (FIG. 5), indicating the complete desorption during each regeneration cycle. Based upon the differential scanning calorimetry (DSC) analysis, energies of 2.67 MJ/kg are needed to release ethylene and regenerate PAF-1-SO3Ag.

Figure 6:
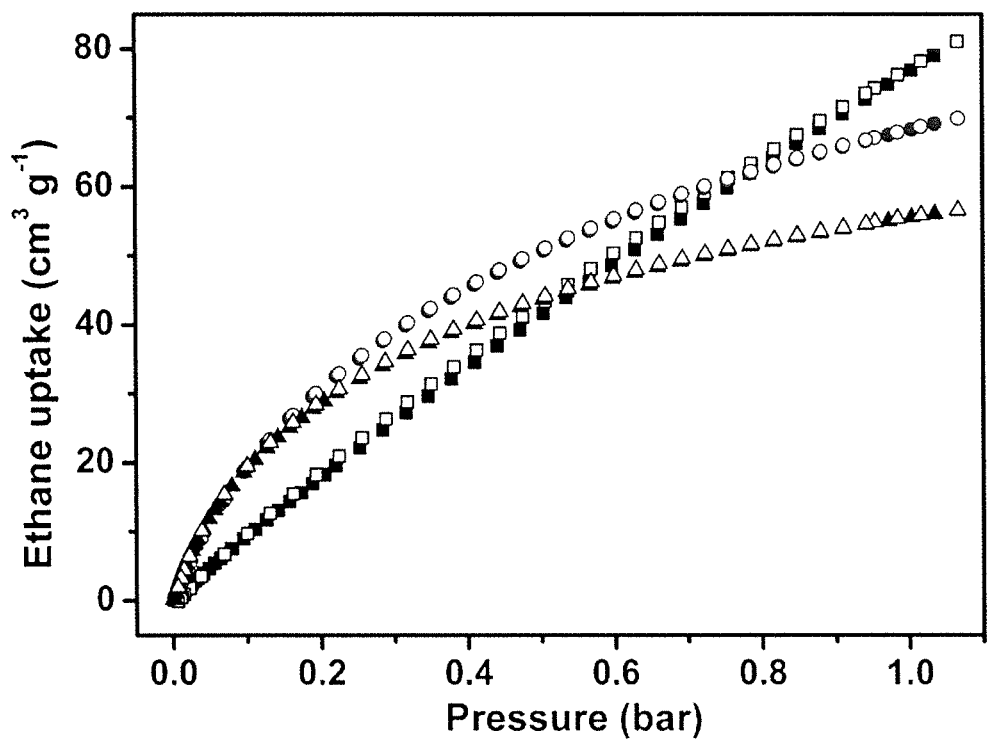
FIG. 6 is a graph of ethane sorption isotherms of crosslinked poly-tetraphenylmethane (PAF-1) (squares), sulfonate-grafted PAF-1 (PAF-1-SO₃H) (circles), and Ag(I) exchanged PAF-1-SO₃H (PAF-1-SO3Ag) (triangles) at 296 K. Filled: adsorption; unfilled: desorption.

Interestingly, different from the ethylene adsorption, the trend of ethane uptake by the three sample follows the order of PAF-1>PAF-1-SO$_3$H>PAF-1-SO$_3$Ag at 296 K and 1 atm (FIG. 6). The smallest ethane uptake amount observed for PAF-1-SO$_3$Ag is primarily attributed to its lower surface area when compared with PAF-1 and PAF-1-SO$_3$H. This result also suggests that the incorporation of Ag(I) ions would not increase ethane uptake capacity.

Calculations of adsorption selectivity. The selectivity of preferential adsorption of C$_2$H$_4$ (component 1) over C$_2$H$_6$ (component 2) in a mixture containing 1 and 2, can be formally defined as $$S_{ads} = \frac{q_1/q_2}{p_1/p_2} \quad (2)$$

In equation (2), q$_1$ and q$_2$ are the component loadings of the adsorbed phase in the mixture. The calculations of S$_{ads}$ are based on the use of the Ideal Adsorbed Solution Theory (IAST) of Myers and Prausnitz. Myers et al., *AIChE J.* 1965, 11:121.

Figure 8:
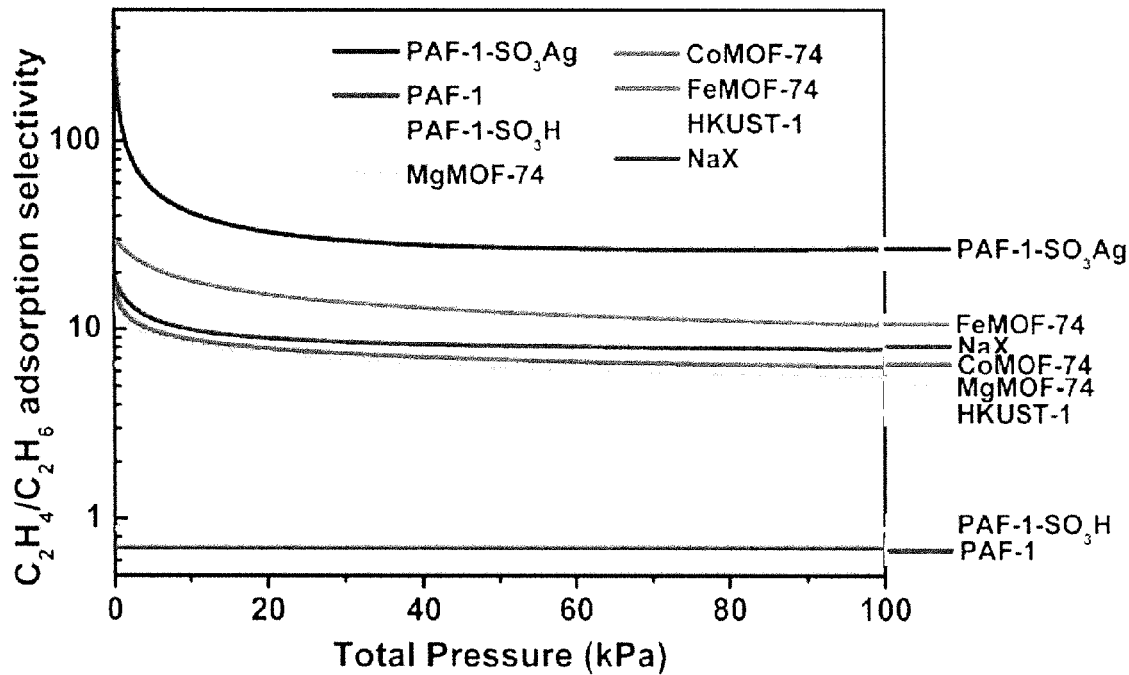
FIG. 8 is a graph of $C_2H_4/C_2H_6$ adsorption selectivities for Ag(I) exchanged sulfonate-grafted cross-linked polytetraphenylmethane (PAF-1-SO₃Ag) and other porous materials at 296 K from ideal adsorbed solution theory.

Ethylene/ethane adsorption selectivities were calculated using ideal adsorbed solution theory (IAST) for PAF-1-SO$_3$Ag, PAF-1, and PAF-1-SO$_3$H (FIG. 8). For an equimolar mixture of ethylene and ethane at 296 K, the adsorption selectivity (S$_{ads}$) obtained for PAF-1-SO$_3$Ag is 27 at 100 kPa, far exceeding those calculated for both PAF-1 (S$_{ads}$=0.7) and PAF-1-SO$_3$H (S$_{ads}$=0.88). The ethylene/ethane adsorption selectivity of PAF-1-SO$_3$Ag at 296 K and 100 kPa is also significantly higher than those of zeolite NaX, the MOFs FeMOF-74 [also known as (a.k.a.) Fe$_2$(dobdc)], CoMOF-74 [a.k.a. Co$_2$(dobdc)], MgMOF-74 [a.k.a. Mg$_2$(dobdc)], CuBTC (a.k.a. HKUST-1) (FIG. 8), and the POP CuA$_{10}$B$_1$, exhibiting ethylene/ethane selectivities of 8, 11, 6.4, 5.6, 3.6, and 3.8 respectively. It's worth noting that the ethylene/ethane adsorption selectivities of PAF-1-SO$_3$Ag are considerably higher than those of zeolite NaX and other MOFs over the entire pressure range with the adsorption selectivity value at 1 kPa (S$_{ads}$=125) even about an order of magnitude higher (FIG. 8).

Figure 9:
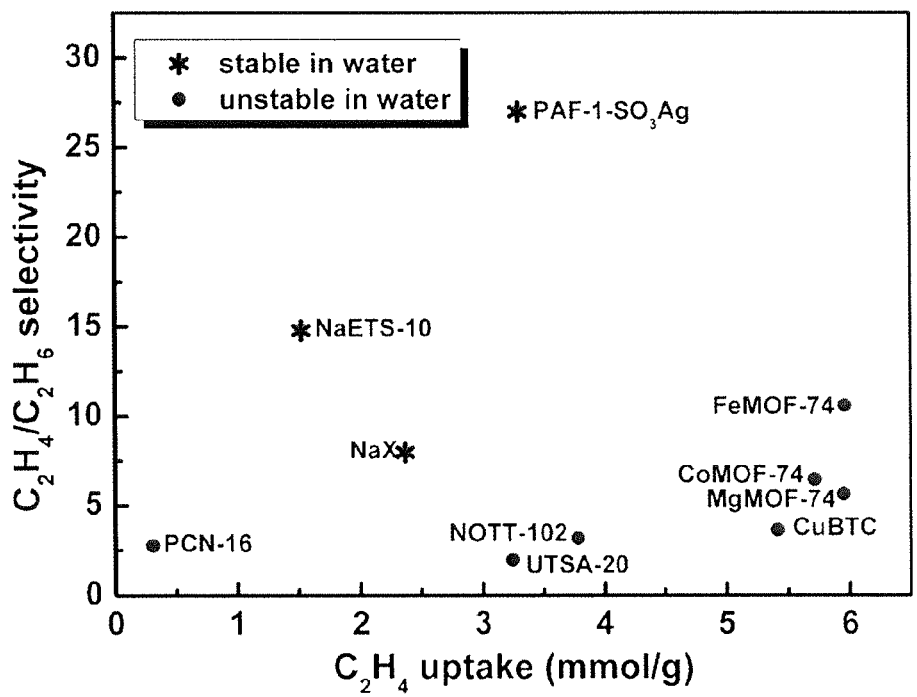
FIG. 9 is a plot of the $C_2H_4/C_2H_6$ adsorption selectivity versus the gravimetric uptake capacity of ethylene for adsorption from an equimolar $C_2H_4/C_2H_6$ mixture at the total bulk gas phase at 296 K and 100 kPa (Note: the uptake capacity of ethylene for FeMOF-74 is at 318 K).
Figure 10:
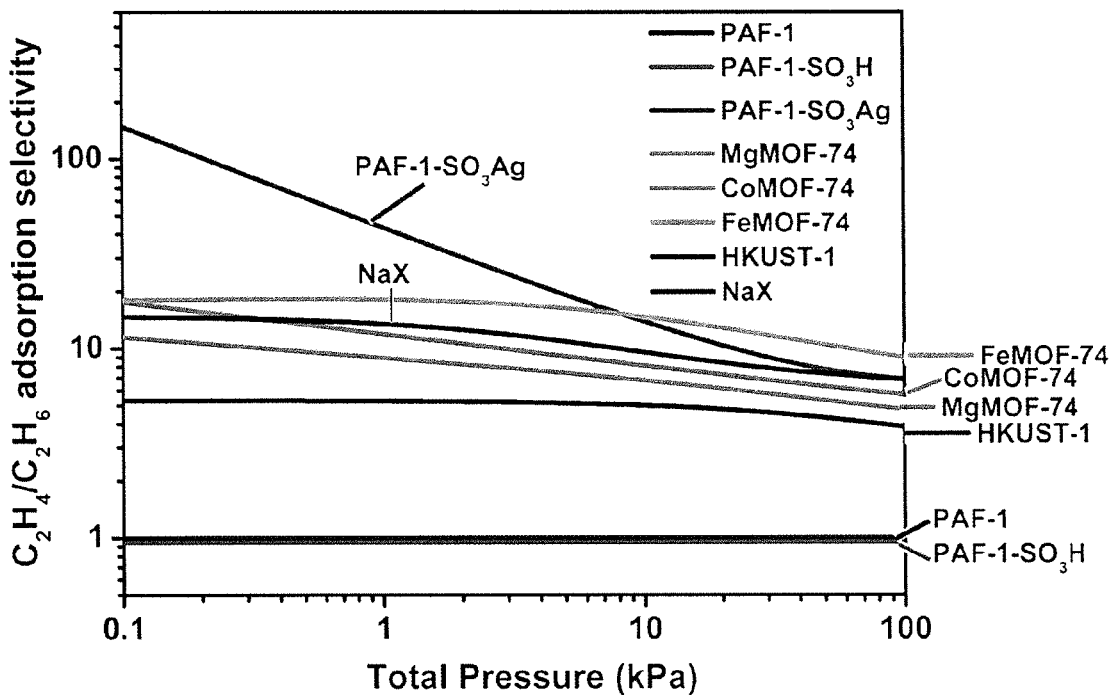
FIG. 10 is a plot of the $C_2H_4/C_2H_6$ adsorption selectivities for Ag(I) exchanged sulfonate-grafted cross-linked polytetraphenylmethane (PAF-1-SO₃Ag) with other porous materials at 318 K.
Figure 11:
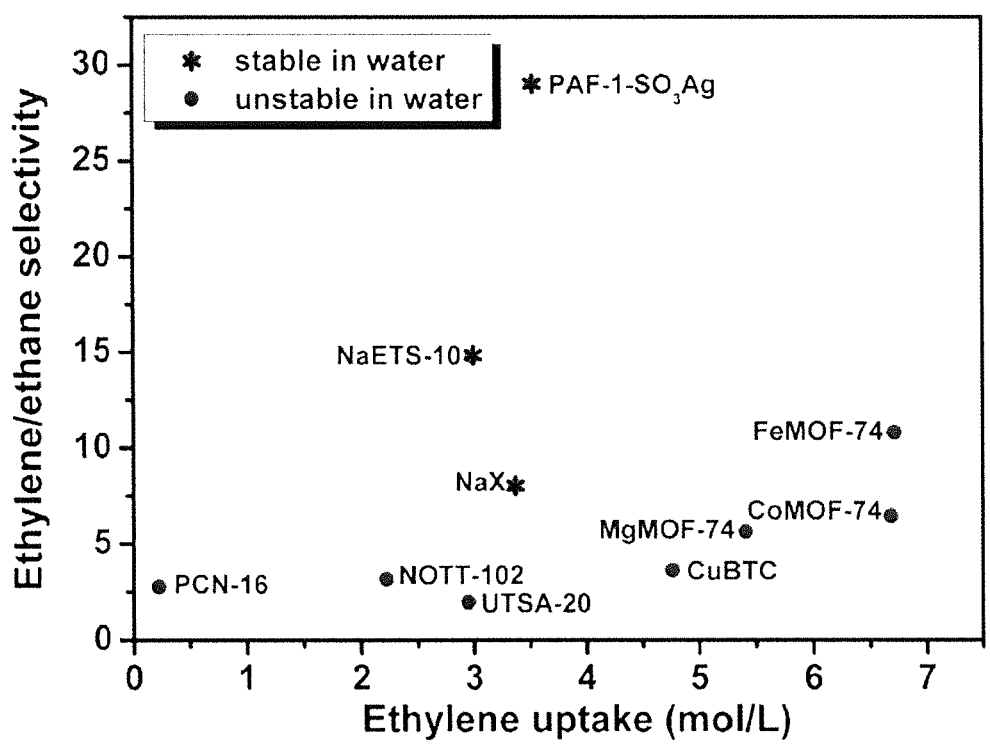
FIG. 11 is a plot of the $C_2H_4/C_2H_6$ adsorption selectivity versus the volumetric uptake capacity of ethylene for adsorption from an equimolar $C_2H_4/C_2H_6$ mixture at the total bulk gas phase at 296 K and 100 kPa. The volumetric uptake capacity of ethylene for PAF-1-SO3Ag is estimated based upon its compressed pellet's density of 1.07 g/cm³; whereas the volumetric uptake capacity of ethylene for others is estimated based upon their respective densities calculated from the crystal structures.

In practice, the combination of adsorption selectivity and uptake capacity of gas mixtures can contribute to the characteristics of ethylene/ethane separation. FIG. 9 shows the IAST calculations of the ethylene/ethane adsorption selectivity versus the gravimetric uptake capacity of ethylene for adsorption from an equimolar ethylene/ethane mixture at the total bulk gas phase at 296 K and 100 kPa for PAF-1-SO$_3$Ag and several benchmark microporous adsorbent materials. Both adsorption selectivity and gravimetric uptake capacity of PAF-1-SO$_3$Ag are significantly higher than two important zeolites of NaETS-10 and NaX. The volumetric ethylene uptake capacity of PAF-1-SO$_3$Ag (FIG. 11), which is estimated based upon the density of compressed PAF-1-SO3Ag pellet, also surpasses that of NaETS-1028 and NaX.19a, 29 Albeit the ethylene uptake capacity of PAF-1-SO3Ag is lower than that of some MOF materials, much higher ethylene adsorption selectivity alongside excellent water stability represent advantages in practice over most MOFs30 investigated so far.

Example 3

Ethylene-Framework Interactions

Fitting of Pure Component Isotherms. The measured experimental isotherm data for C$_2$H$_4$, and C$_2$H$_6$ on PAF-1-SO$_3$Ag were fitted with the dual-Langmuir-Freundlich isotherm model $$q = q_{A,sat}\frac{b_A p^{v_A}}{1+b_A p^{v_A}} + q_{B,sat}\frac{b_B p^{v_B}}{1+b_B p^{v_B}} \quad (1)$$

Figure 12:
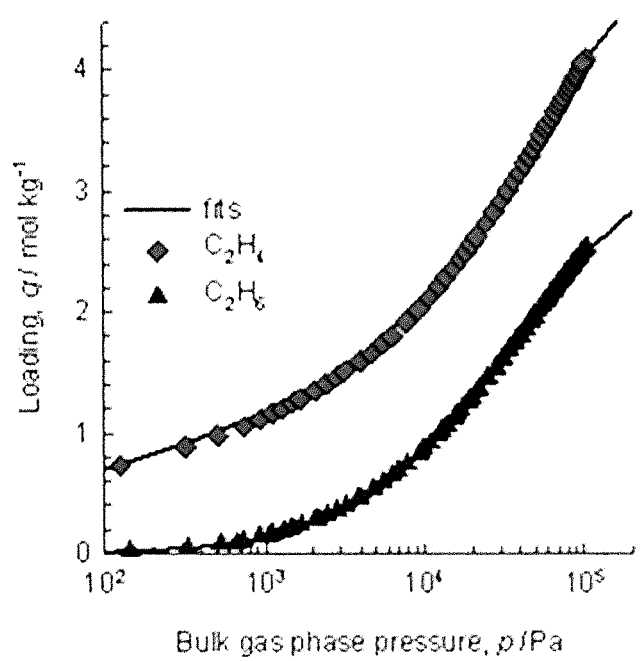
FIG. 12 is a graph comparing the experimentally determined component loadings for $C_2H_4$ and $C_2H_6$ on PAF-1-SO3Ag at 296 K with the isotherm fits using parameters specified in Table 1.

The fit parameters for C$_2$H$_4$ and C$_2$H$_6$ are specified in Table 1. FIG. 12 presents a comparison of the experimentally determined component loadings for C$_2$H$_4$ and C$_2$H$_6$ on PAF-1-SO$_3$Ag at 296 K with the isotherm fits using parameters specified in Table S1. The fits are excellent over the entire range of pressures.

TABLE 1

Dual-Langmuir-Freundlich fits for C$_2$H$_4$ and C$_2$H$_6$ at 296 K in PAF-1-SO$_3$Ag.

| | Site A | | | Site B | | |
|---|---|---|---|---|---|---|
| | $q_{i,A,sat}$ mol/kg | $b_{i,A}$ Pa$^{-v_i}$ | $v_{i,A}$ dimensionless | $q_{i,B,sat}$ mol/kg | $b_{i,B}$ Pa$^{-v_i}$ | $v_{i,B}$ dimensionless |
| C$_2$H$_4$ | 3.6 | 5.86 × 10$^{-5}$ | 0.9 | 2 | 1.05 × 10$^{-1}$ | 0.35 |
| C$_2$H$_6$ | 3.4 | 8.35 × 10$^{-5}$ | 0.9 | | | |

The pure component isotherm data for PAF-1, and PAF-1-SO$_3$H could be fitted with single site Langmuir model; the fit parameters are provided in Table 2, and Table 2, respectively.

TABLE 2

Langmuir fits for C$_2$H$_4$ and C$_2$H$_6$ at 296 K in PAF-1.

| | Site A | | |
|---|---|---|---|
| | $q_{i,A,sat}$ mol/kg | $b_{i,A}$ Pa$^{-v_j}$ | $v_{i,A}$ dimensionless |
| C$_2$H$_4$ | 15 | 2.04 × 10$^{-6}$ | 1 |
| C$_2$H$_6$ | 15 | 2.91 × 10$^{-6}$ | 1 |

TABLE 3

Langmuir fits for C$_2$H$_4$ and C$_2$H$_6$ at 296 K in PAF-1-SO$_3$H.

| | Site A | | |
|---|---|---|---|
| | $q_{i,A,sat}$ mol/kg | $b_{i,A}$ Pa$^{-v_j}$ | $v_{i,A}$ dimensionless |
| C$_2$H$_4$ | 4.5 | 1.87 × 10$^{-5}$ | 1 |
| C$_2$H$_6$ | 4.5 | 2.12 × 10$^{-5}$ | 1 |

Estimation of Isosteric Heats of Adsorption, $Q_{st}$. The isosteric heat of adsorption, $Q_{st}$, were calculated using the Clausius-Clapeyron equation by differentiation of the dual-Langmuir-Freundlich fits of the isotherms at two different temperatures, 296 K and 318 K with T-dependent parameters.

$$Q_{S_t} = RT^2 \left( \frac{\partial \ln p}{\partial T} \right)_q \quad (3)$$

Figure 13:
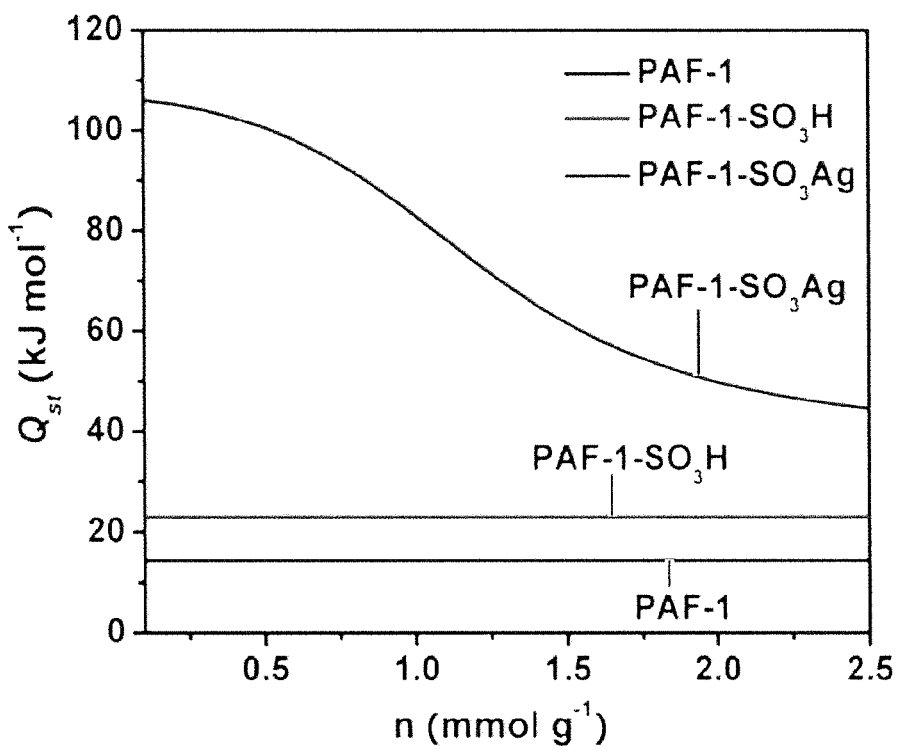
FIG. 13 is a graph of the isosteric heats adsorption, $Q_{st}$ of $C_2H_4$ for PAF-1, PAF-1-SO3H, and PAF-1-SO3Ag.
Figure 14:
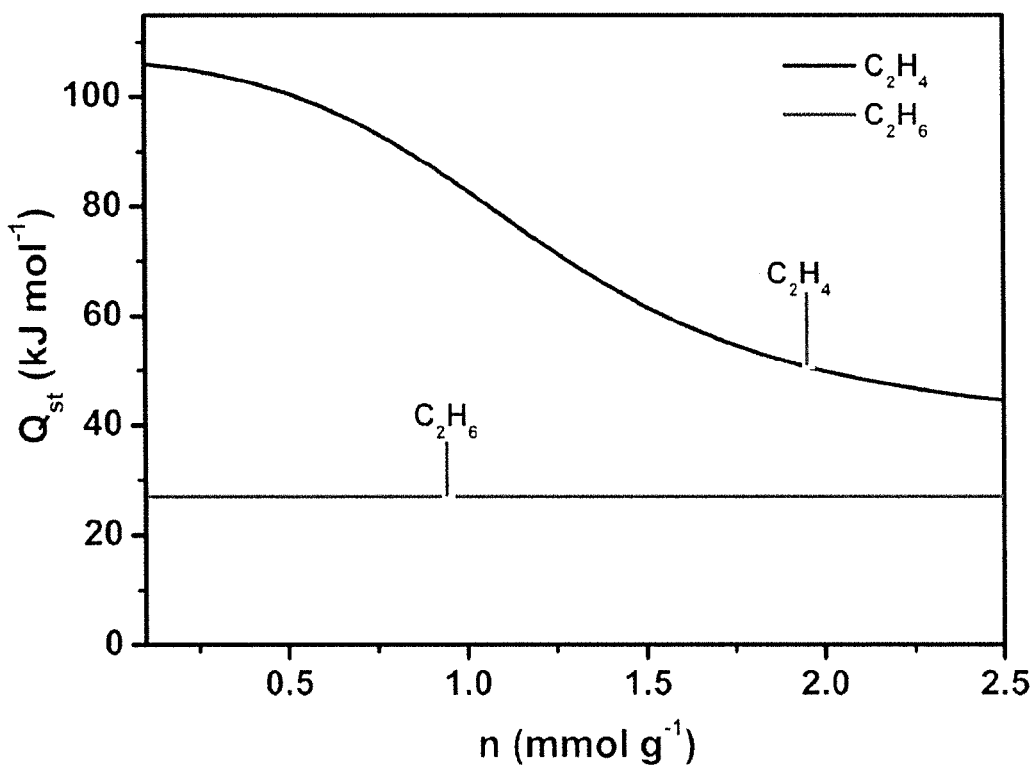
FIG. 14 is a graph of the isosteric heats of adsorption for ethylene (black) and ethane (red) in PAF-1-SO3Ag.

The exceptional ethylene adsorption properties of PAF-1-SO$_3$Ag can stem from the strong interactions between ethylene molecules and the framework of PAF-1-SO$_3$Ag as a result of the formation of π-complexation between the d orbitals of Ag(I) and the pi orbitals of carbon-carbon double bonds in ethylene. The isosteric heats of adsorption ($Q_{st}$) based upon Clausius-Clapeyron equation by differentiation of the dual-Langmuir-Freundlich fits of the isotherms at two different temperatures, 296 K and 318 K with T-dependent parameters. As shown in FIG. 13, at close to zero loading, the $Q_{st}$ for ethylene in PAF-1-SO$_3$Ag is 106 kJ·mol$_{-1}$, remarkably higher than that of PAF-1 (14 kJ·mol$^{-1}$) and PAF-1-SO$_3$H (23 kJ·mol$^{-1}$). The $Q_{st}$ for ethylene in PAF-1-SO$_3$Ag is consistent with that observed in other Ag(I)-based π-complexation systems, suggesting the formation of π-complexation between the ethylene molecules and Ag(I) ions in PAF-1-SO$_3$Ag. The $Q_{st}$ exceeds that in MOFs with open metal sites, e.g. FeMOF-74 (45 kJ·mol$^{-1}$) or (47 kJ·mol$^{-1}$), MgMOF-74 (42 kJ·mol$^{-1}$), CoMOF-74 (41 kJ·mol$^{-1}$), CuBTC (39 kJ·mol$^{-1}$). These results highlight that, compared with open metal sites, Ag(I) ions can boost the interactions with ethylene molecules more in a porous framework via the formation of π-complexation. In contrast with the high $Q_{st}$ for ethylene, PAF-1-SO$_3$Ag shows a significantly lower $Q_{st}$ for ethane with a value of 27 kJ·mol$^{-1}$ (FIG. 14); thus validating that the Ag(I) ions serve as a preferential binding sites, selectively adsorbing ethylene over ethane thereby resulting in high ethylene/ethane adsorption selectivities.

To further prove the formation of 7-complexation between the ethylene molecules and Ag(I) ions in PAF-1-SO$_3$Ag, in situ IR measurements of ethylene adsorption at room temperature were conducted. The —CH2 out-of plane wagging mode at 949 cm$^{-1}$ was found as the most sensitive mode, responding to the interaction between ethylene and the substrate surface. Ethylene adsorption on PAF-1 and PAF-1-SO$_3$H exhibited IR features similar to that of gas phase C$_2$H$_4$, indicating a weak interaction, which is further evidenced by the complete removal of ethylene IR features after room temperature desorption in helium purge. In contrast, upon initial adsorption PAF-1-SO$_3$Ag shows strongly perturbed CH$_2$ mode at 980 cm$^{-1}$. The intensity is even comparable with the gas-phase mode at 949 cm$^{-1}$ at saturation. Two extra IR features at 1960 cm$^{-1}$ (combination mode of —CH$_2$ wagging) and 1634 cm$^{-1}$ (C=C stretching), not observed on the PAF-1 and PAF-1-SO$_3$H, were observed in the IR, further confirming ethylene adsorption on PAF-1-SO$_3$Ag. These new IR bands due to adsorbed ethylene persist well after room temperature desorption, indicating a strong interaction between ethylene and PAF-1-SO$_3$Ag. The blue-shift of the —CH$_2$ wagging mode can be attributed to the combinative d-π and d-π* interaction between Ag and ethylene, thus confirming the formation of 7-complexation between the ethylene and Ag(I) ions in PAF-1-SO$_3$Ag.

Example 4

Ethylene/Ethane Breakthrough Experiments And Simulations

Figure 15:
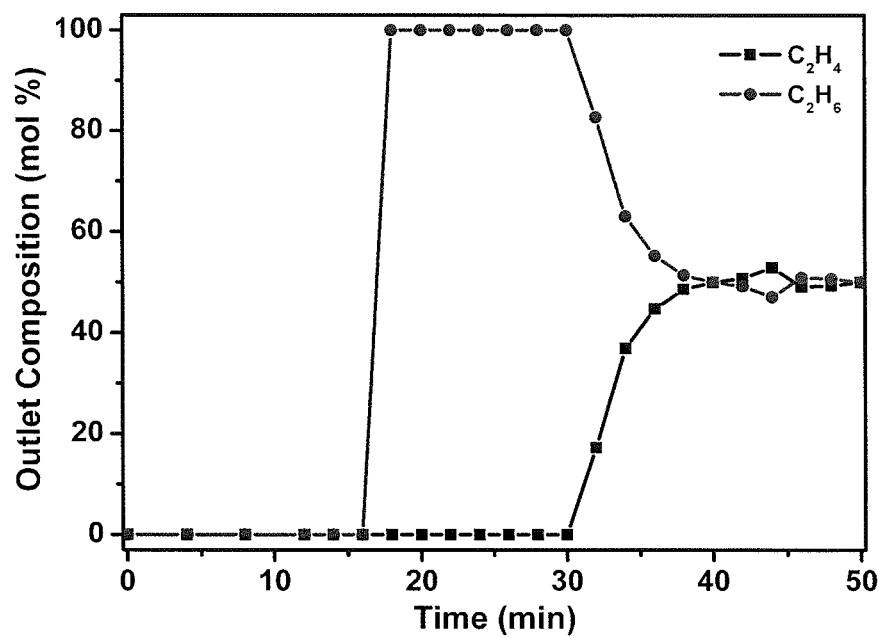
FIG. 15 is a graph of the experimental data on transient breakthrough of an equimolar $C_2H_4/C_2H_6$ mixture in an adsorber bed packed with Ag(I) exchanged sulfonate-grafted cross-linked poly-tetraphenylmethane (PAF-1-SO₃Ag) in the adsorption phase of a Pressure Swing Adsorption (PSA) operation.

To evaluate the performance of PAF-1-SO$_3$Ag in an actual adsorption-based separation process, breakthrough experiments were performed in which an equimolar ethylene/ethane mixture was flowed over a packed bed of the solid with a total flow of 2 mL/min at 296 K. As shown in FIG. 15, PAF-1-SO$_3$Ag can effectively separate an equimolar mixture of ethylene and ethane into the pure component gases of greater than 99% purity.

In a typical experiment, 400 mg of PAF-1-SO$_3$Ag were swiftly grounded and packed into a quartz column (6 mm I.D.×220 mm) with silica wool filling the void space. The sample was in-situ activated under vacuum (6.5×10$^{-4}$ Pa) at 110° C. for 2 hours. Then, Helium flow (2 ml/min) was introduced the system to purge the adsorbent until the temperature of the column was decreased to 23° C. The breakthrough test was started by introducing 1:1 C$_2$H$_4$/C$_2$H$_6$ mixture gas at total flow rate of 2.0 ml/min and switching off the He gas. Effluent from the column was monitored using a GC with a flame ionization detector. The dead volume of this setup was determined to be 18.6 cm$^3$. We also carried out breakthrough simulations for C$_2$H$_4$/C$_2$H$_6$ mixtures in a fixed bed to further demonstrate the feasibility of producing 99.95%+pure C$_2$H$_4$ in a Pressure Swing Adsorption (PSA) operation. The simulated breakthrough curves were in good agreement with the experimental data. During the adsorption cycle, C$_2$H$_6$ at purities >99% can be recovered for a certain duration of the adsorption cycle. In addition, ethylene of 99.95%+purity, required as feedstock to the polymerization reactor, can also be recovered.

We claim:

1. A composition for olefin separation comprising a porous organic polymer (POP) having incorporated therein a plurality of monovalent metal cations,
   wherein the porous organic polymer is a porous aromatic framework, and
   wherein the monovalent metal cation is Cu(I) or Ag(I).

2. The composition of claim 1, wherein the composition has an ethylene uptake capacity of 70 cm$^3$ g$^{-1}$ to 200 cm$^3$ g$^{-1}$ at 1 atm and 296 K.

3. The composition of claim 1, wherein the composition has an ethylene/ethane adsorption selectivity of 20 to 500 at 296 K.

4. The composition of claim 1, wherein the composition has an ethylene uptake capacity that is stable and recyclable.

5. The composition of claim 1, wherein the porous organic polymer is stable under basic conditions.

6. The composition of claim 1, wherein the porous organic polymer has a surface area from 20 m$^2$/g to 8,000 m$^2$/g.

7. The composition of claim 1, wherein the porous organic polymer has a pore size from 5 angstroms to 500 angstroms.

8. The composition of claim 1, wherein the porous organic polymer comprises a monomer unit comprising an aryl moiety.

9. The composition of claim 8, wherein the aryl moiety is selected from the group consisting of substituted and unsubstituted benzene, naphthalene, anthracene, biphenyl, pyridine, pyrimidine, pyridazine, pyrazine and triazine.

10. The composition of claim 1, wherein the porous organic polymer comprises a monomer unit comprising an acidic functional group,
wherein the monovalent metal cations are associated covalently or non-covalently with the acidic functional group.

11. The composition of claim 10, wherein the acidic functional group is selected from the group consisting of sulfonate, phosphonate, and phosphonocarboxylate.

12. The composition of claim 10, wherein at least 50% of the acidic functional groups are associated with one of the monovalent metal cations.

13. The composition of claim 1, wherein the porous aromatic framework comprises cross-linked poly-tetraphenylmethane.

14. The composition of claim 1, wherein the porous organic polymer comprises cross-linked poly-tetraphenylmethane that has been grafted with sulfonate groups;
wherein the monovalent metal cations are Ag(I) cations that are associated non-covalently with the sulfonate groups.

15. A method of making the compositions of any one of claims 1-12, 13, and 14, the method comprising:
synthesizing a porous organic polymer;
grafting acidic functional groups onto the porous organic polymer; and
cation exchange with a salt of a monovalent metal cation,
wherein the porous organic polymer is a porous aromatic framework, and
wherein the monovalent metal cation is Cu(I) or Ag(I).

16. A method of separating or enriching a mixture of olefins and paraffins comprising passing a feedstock solution containing the olefins and paraffins across the composition of any one of claims 1-12, 13, and 14.

17. The method of claim 16, wherein the mixture comprises ethylene and ethane, and
wherein the ethylene, the ethane, or both are purified to greater than 99%.

18. The method of claim 16, wherein the composition has an olefin uptake capacity of 70 cm$^3$ g$^{-1}$ to 200 cm$^3$ g$^{-1}$ at 1 atm and 296 K.

19. The method of claim 16, wherein the composition has an olefin/paraffin adsorption selectivity of 20 to 500 at 296 K.

20. The method of claim 16, wherein the composition has an olefin uptake efficiency that is at least 50% more than the olefin uptake efficiency of the otherwise same composition under the otherwise same conditions except where the monovalent metal cations have been replaced by hydrogen cations.

* * * * *